United States Patent [19]

Ogawa et al.

[11] Patent Number: 5,137,726

[45] Date of Patent: Aug. 11, 1992

[54] EMULSIFIABLE PESTICIDAL SOLID COMPOSITIONS

[75] Inventors: Masao Ogawa, Toyonaka; Shigenori Tsuda, Kyoto; Kozo Tsuji, Nara, all of Japan

[73] Assignee: Sumitomo Chemical Company, Limited, Osaka, Japan

[21] Appl. No.: 509,581

[22] Filed: Apr. 16, 1990

[30] Foreign Application Priority Data

Apr. 26, 1989 [JP] Japan .................................. 1-108224
Feb. 27, 1990 [JP] Japan .................................. 2-048848

[51] Int. Cl.$^5$ ............................................ A01N 25/00
[52] U.S. Cl. .................................. 424/405; 424/408; 424/409
[58] Field of Search ................................ 424/78, 405

[56] References Cited

U.S. PATENT DOCUMENTS

| | | | |
|---|---|---|---|
| 3,639,617 | 2/1972 | King . | |
| 4,313,847 | 2/1982 | Chasin et al. | 514/786 |
| 4,434,077 | 2/1984 | Kaneko | 524/386 |
| 4,844,734 | 7/1989 | Iwasaki et al. | 514/786 |
| 4,875,929 | 10/1989 | Morgan et al. | 71/93 |
| 4,892,889 | 1/1990 | Kirk | 514/786 |

FOREIGN PATENT DOCUMENTS 57-109702  7/1982  Japan .
60-36402   2/1985  Japan .

OTHER PUBLICATIONS

Patent Abstracts of Japan, vol. 4, No. 30 (C-2) [512], 15 Mar. 1980, The Patent Office Japanese Government, Tokyo, JP; & JP-A-55 004 336 (Kiyouritsu Sanitarii K.K.) Dec. 1, 1980.

Central Patents Index, Basic Abstracts Journal, section C, AGDOC, 16 Apr. 1980, AN=13757C/08, Derwent Publications Ltd, Londres, GB; & JP-a-55 004 336 (Kiyouritsu Sanitarii K.K.) Dec. 1, 1980.

*Primary Examiner*—Thurman K. Page
*Assistant Examiner*—Peter F. Kulkosky
*Attorney, Agent, or Firm*—Stevens, Davis, Miller & Mosher

[57] ABSTRACT

The present invention discloses emulsifiable pesticidal solid compositions obtained by spray-drying aqueous emulsions comprising (a) pesticides having a melting point of not higher than 70° C., (b) surfactants, (c) dextrin and/or lactose, and (d) water and, if necessary and desired, (e) organic solvents and/or water soluble carriers. The emulsifiable pesitcidal solid compositions are easy in handling and can be readily emulsified.

6 Claims, No Drawings

EMULSIFIABLE PESTICIDAL SOLID COMPOSITIONS

The present invention relates to emulsifiable pesticidal solid compositions which can be readily emulsified, when diluted with water upon use.

Emulsifiable concentrates of pesticides are uniform solutions obtained by dissolving pesticides and surfactants in organic solvents. The emulsifiable concentrates are general formulations which are easy in handling and can stably exhibit their effects.

However, since the emulsifiable concentrates contain organic solvents in large quantities, problems of environmental pollution, malodor, inflammability, etc., due to vaporization of the organic solvent, are involved. In addition, these formulations have sometimes such problems as phytotoxicity to crops due to the solvents.

To solve these problems, various investigations have been hitherto made to make emulsifiable concentrates into a powdery form. For example, there is reported a method which comprises absorbing an emulsifiable concentrate onto a carrier such as starch, cellulose powders, urea, cork powders, in organic silicates, type II anhydrous gypsum, etc. In conventional techniques, however, where there encounter problems that an absorbability of emulsifiable concentrate onto the carriers is too small to prepare emulsifiable pesticidal solid composition which has good flowability, or emulsifiability is insufficient when diluted with water.

Furthermore, there are proposed emulsifiable dry powders of pesticides characterized by uniformly absorbing emulsifiable concentrates comprising pesticides and surfactants to dry powders of starch hydrolysate (i.e., dextrin) having a glucose content (abbriviation, DE) below 18 (Japanese Patent Application Laid-Open No. 57-109702). However, the emulsifiable dry powders encounter problems that liquid readily tends to be exudated, the preparation is sticky with an amount of oil-absorbing emulsifiable concentrate exceeding 30% so that its flowability seriously decreases, and with the amount exceeding 50%, it is substantially impossible to prepare commercially available preparations, etc.

In the case of solid formulations containing mineral carriers, a problem is involved in that when the formulations are diluted with water and sprayed over fruit trees, fruits are stained with the mineral carriers to decrease commercial value.

In order to obtain excellent emulsifiable pesticidal solid compositions, the present inventors have made various investigations and as a result, they have found emulsifiable pesticidal solid compositions which are not sticky and have good flowability even though the content of oil-absorbing emulsifiable concentrate is high and which can be readily emulsified. The present invention has thus be accomplished.

That is, the present invention provides emulsifiable pesticidal solid compositions prepared by a spray dry method from aqueous emulsions comprising (a) pesticides having a melting point of not higher than 70° C., (b) surfactants, (c) dextrin and/or lactose, and (d) water and, if necessary and desired, (e) organic solvents and/or water soluble carriers.

In general, it is difficult to solidify pesticides in a liquid form at room temperature. It is also difficult to solidify even pesticides which have melting points around room temperature. In addition, these pesticides involve a problem in storage stability even if they are prepared into a solid form. According to the present invention, however, excellent emulsifiable pesticidal solid compositions can be obtained even if the pesticides have a melting point of 70° C. or below.

The pesticide as used herein not only refers to a single compound but also include a mixture of two or more compounds. In the case of mixture, the present invention is directed to a mixture showing a melting point of not higher than 70° C.

Any surfactants can be used as the surfactant in the present invention, so long as they can emulsify pesticides, or pesticides and organic solvents. Examples of such surfactants include glycerine fatty acid esters, sucrose fatty acid esters, sorbitan fatty acid esters, fatty acid salts, alkyl sulfates, alkylbenzene sulfonic acid salts, alkyl aryl ethers and polyoxyethylenated products thereof, ethylene oxide addition products of higher alcohol; polyoxyethylene polyoxypropylene glycol, lignine sulfonic acid salt, polyoxyethylene styrylphenyl ether, polyoxyethylene alkyl esters, alkyl aryl sulfates, etc. These surfactants may be used singly or in a suitable combination. An amount of the surfactant added is generally in a range of 0.1 to 20 wt%, preferably in a range of 1 to 10 wt%, based on the total weight of the composition. Surfactants which become liquid by heating and can uniformly mix with pesticides, or pesticides and organic solvents are preferred but it is not always necessary to use such surfactants. It is sufficient that surfactants be dissolved in water when the preparation is diluted with water. Heat-stable surfactants are more preferred.

Where a melting point of pesticide is in a range of 0 to 70° C. or where surfactants are in a paste or solid form at room temperature, a small quantity of solvent may also be added to the composition, if necessary and desired, for purposes of reducing a viscosity upon preparation and preventing crystallization of the pesticides in the composition when stored at a low temperature. As the solvent, non-volatile solvents or low volatile solvents are used. Examples of such solvents used to regulate the viscosity and prevent crystrallization of pesticides in the composition include those uniformly mixed together with pesticides, for example, vegetable oil, mineral oil, liquid paraffin, aromatic hydrocarbons such as phenylxylylethane, etc.; ketones; polyethylene glycol which have a average molecular weight of 200 to 600 and are liquid at room temperature, polypropylene glycol, glycol ethers, etc. Of these, phenylxylylethane is preferred in view of its boiling point, inflammability, and the like. An amount of the solvent is generally in a range of 10 to 1000 wt%, preferably in a range of 30 to 200 wt%, based on the pesticide.

Examples of lactose which can be used in the present invention include hydrated α-lactose, anhydrous α-lactose, anhydrous β-lactose, etc. Taking stability of the preparation into account, hydrated α-lactose is preferred.

Examples of dextrin which can be used in the present invention are decomposition products obtained by subjecting naturally occurring starches such as potato starch, corn starch, sweet corn starch, sweet potato starch, wheat starch, rice starch, tapioca starch, sago starch, etc., various processed starches such as amylose or amylopectin fractionation products, etherated starch, esterified starch, crosslinked starch, oxidized starch, acid treated starch, grafted starch, etc. and their derivatives, to acid decomposition, alkali decomposition, enzymatic decomposition or hydrolysis in combination thereof, in a conventional manner. The decomposition products are generally used as containing DE of less than 40, ordinarily DE of 2 to 40. In view of hygroscopic property of the composition and stability of emulsified products, etc., those having DE of 5 to 30 are particularly preferred.

The term DE as used herein refers to a proportion of reducing sugar in the anhydrous solid content. The content of reducing sugar is determined by the Fehling-Lehman-Schor method in accordance with the description in "JIKKEN NOGEI KAGAKU (Experimental Agricultural Chemistry)" (revised version), second volume, pages 638–639 and Table 3 attached (published by Asakura Shoten Publishing Co., 1963).

The amount of dextrin and/or lactose is generally in a range of 5 to 90 wt%, preferably in a range of 10 to 80 wt%, based on the total weight of the composition.

In preparing the emulsion in the present invention by emulsifying pesticides, or pesticides and organic solvents in water together with surfactants, dextrin and/or lactose, water soluble carriers may also be added to the composition. Examples of the water soluble carrier which can be used include water soluble polymers such as polyvinyl alcohol, methyl cellulose, hydroxypropyl cellulose, carboxymethyl cellulose sodium, gelatin, gum arabic, dextran, sodium alginate, sodium polyacrylate, etc.; urea, ammonium sulfate, sucrose, sodium chloride, Glauber's salt, etc. These water soluble carriers may be appropriately added in such an amount that they are soluble in aqueous emulsion upon preparation of the emulsifiable pesticidal solid compositions in accordance with the present invention and a concentration of the carriers in a spray mix prepared upon sprinkling is less than the solubility in a dilution magnification.

In addition to pesticides, surfactants, dextrin, lactose, organic solvents and water soluble carriers, the emulsifiable pesticidal solid compositions in accordance with the present invention may also appropriately contain stabilizers, synergists, coloring agents, etc.

However, mineral carriers should not be added, in view of the nature that the preparations are emulcifiable pesticidal solid compositions.

The emulsifiable pesticidal solid compositions in accordance with the present invention are used to exterminate or control harmful organisms or regulate plant growth.

The emulsifiable pesticidal solid compositions in accordance with the present invention are spread as they are or after diluting with water. When diluted with water, its dilution magnification varies depending upon kind of pesticide, kind of harmful organism to be controlled, blight to be applied, herbs to be applied, crops to be applied, time period for treatment, method, etc. and is not decisively given but is generally in a range of from 20 to 10,000 times.

Specific examples of the pesticides which can be used in the present invention are given below but the present invention is not deemed to be limited only to these examples.

| Compound No. | Compound |
|---|---|
| (1) | α-Cyano-3-phenoxybenzyl 2-(4-chlorophenyl)-3-methylbutyrate |
| (2) | (S)-α-Cyano-3-phenoxybenzyl (S)-2-(4-chlorophenyl)-3-methylbutyrate |
| (3) | α-Cyano-3-phenoxybenzyl 2,2,3,3-tetramethylcyclopropanecarboxylate |
| (4) | 3-Phenoxybenzyl 3-(2,2-dichlorovinyl)-2,2-dimethylcyclopropanecarboxylate |
| (5) | 3-Phenoxybenzyl chrysanthemate |
| (6) | α-Cyano-3-phenoxybenzyl 3-(2,2-dichlorovinyl)-2,2-dimethylcyclopropanecarboxylate |
| (7) | α-Cyano-3-(4-bromophenoxy)benzyl 3-(2,2-dichlorovinyl)-2,2-dimethylcyclopropanecarboxylate |
| (8) | α-Cyano-3-(4-fluorophenoxy)benzyl 3-(2,2-dichlorovinyl)-2,2-dimethylcyclopropanecarboxylate |
| (9) | α-Cyano-3-(3-bromophenoxy)benzyl 3-(2,2-dichlorovinyl)-2,2-dimethylcyclopropanecarboxylate |
| (10) | α-Cyano-3-(4-chlorophenoxy)benzyl 3-(2,2-dichlorovinyl)-2,2-dimethylcyclopropanecarboxylate |
| (11) | α-Cyano-3-phenoxybenzyl chrysanthemate |
| (12) | α-Cyano-3-(3-bromophenoxy)benzyl 2-(4-chlorophenyl)-3-methylbutyrate |
| (13) | α-Cyano-3-(3-bromophenoxy)benzyl 2-(4-chlorophenyl)-3-methylbutyrate |
| (14) | α-Cyano-3-(4-chlorophenoxy)benzyl 2-(4-chlorophenyl)-3-methylbutyrate |
| (15) | α-Cyano-3-(4-fluorophenoxy)benzyl 2-(4-chlorophenyl)-3-methylbutyrate |
| (16) | α-Cyano-3-phenoxybenzyl 2-(4-bromophenoxy)-3-methylbutyrate |
| (17) | α-Cyano-3-phenoxybenzyl 2-(4-tertbutyl-phenyl)-3-methylbutyrate |
| (18) | α-Cyano-3-phenoxybenzyl 2-(3,4-methylenedioxyphenyl)-3-methylbutyrate |
| (19) | α-Cyano-(4-fluoro-3-phenoxy)benzyl 3-(2,2-dichlorovinyl)-2,2-dimethylcyclopropanecarboxylate |
| (20) | α-Cyano-3-phenoxybenzyl 2-chloro-4-(trifluoromethyl)anilino-3-methylbutyrate |
| (21) | α-Cyano-3-phenoxybenzyl 2-(4-difluoromethoxyphenyl)-3-methylbutyrate |
| (22) | Cyano-(5-phenoxy-2-pyridyl)methyl 3-(2,2-dichlorovinyl)-2,2-dimethylcyclopropanecarboxylate |
| (23) | α-Cyano-3-phenoxybenzyl 2,2-dimethyl 3-(1,2,2,2-tetrabromoethyl)cyclopropanecarboxylate |
| (24) | α-Cyano-3-phenoxybenzyl 2,2-dimethyl 3-(1,2-dichloro-2,2-dibromoethyl)cyclopropanecarboxylate |
| (25) | α-Cyano-3-phenoxybenzyl 1-(4-ethoxyphenyl)-2,2-dichlorocyclopropanecarboxylate |
| (26) | α-Cyano-3-phenoxybenzyl 2,2-dimethyl 3-(2-chloro-3-trifluoromethylvinyl)cyclopropanecarboxylate |
| (27) | 2-(4-Ethoxyphenyl)-2-methyl propyl 3-phenoxybenzyl ether |
| (28) | 3-Phenoxybenzyl 2-(4-ethoxyphenyl)-3,3,3-trifluoropropyl ether |
| (29) | α-Cyano-3-phenoxybenzyl 2-(2-chloro-4-trifluoromethylanilino)-3-methylbutyrate |
| (30) | α-Cyano-3-phenoxybenzyl 2-(4-difluoromethoxyphenyl)-3-methylbutyrate |
| (31) | 2-Methyl-3-phenylbenzyl (1R,trans)-2,2-dimethyl-3-(2-chloro-2-trifluoromethylvinyl)cyclopropanecarboxylate |
| (32) | 2,3,5,6-Tetrafluoro-4-methylbenzyl (1R,trans)-2,2-dimethyl-3-(2-chloro-2-trifluoromethylvinyl)cyclopropanecarboxylate |
| (33) | 3,4,5,6-Tetrahydrophthalimidomethyl chrysanthemate |
| (34) | 3,4,5,6-Tetrahydrophthalimidomethyl (1R)-chrysanthemate |
| (35) | 3-Allyl-2-methyl-4-oxocyclopent-2-enyl chrysanthemate |
| (36) | 3-Allyl-2-methyl-4-oxocyclopent-2-enyl (1R)-chrysanthemate |
| (37) | (S)-2-Methyl-4-oxo-3-(2-propynyl)-cyclopent-2-enyl (1R)-chrysanthemate |
| (38) | 1-Ethynyl-2-methyl-2-pentenyl (1R)-chrysanthemate |
| (39) | 5-Benzyl-3-furylmethyl chrysanthemate |
| (40) | 5-Benzyl 3-furylmethyl (1R)-chrysanthemate |

-continued

| Compound No. | Compound |
|---|---|
| (41) | O,O-Dimethyl-O-(3-methyl-4-nitrophenyl)-phosphorothioate |
| (42) | O,O-Dimethyl-S-[1,2-di(ethoxycarbonyl)-ethyl]phosphorothioate |
| (43) | O,O-Dimethyl-O-(4-cyanophenyl)phosphorothioate |
| (44) | O,O-Dimethyl-S-(α-ethoxycarbonylbenzyl)-phosphorothioate |
| (45) | O,O-Dimethyl-O-(2-isopropyl-4-methyl-6-pyrimidinyl)phosphorothioate |
| (46) | O,O-Dimethyl-O-[3-methyl-4-(methylthio)-phenyl]phosphorothioate |
| (47) | O-(4-Bromo-2,5-dichlorophenyl)-O,O-diethyl-phosphorothioate |
| (48) | 2-Methoxy-4H-1,3,2-benzodioxa-phospholine-2-sulfide |
| (49) | O,O-Dimethyl-O-(2,4,5-trichlorophenyl)-phosphorothioate |
| (50) | O,O-Dimethyl-O-(3,5,6-trichloro-2-pyridyl)-phosphorothioate |
| (51) | O,O-Dimethyl-O-(3,5,6-trichloro-2-pyridyl)-phosphorothioate |
| (52) | O-(4-Bromo-2,5-dichlorophenyl)-O,O-dimethylphosphorothioate |
| (53) | O,O-Dimethyl-S-(N-methylcarbamoylmethyl)-phosphorodithioate |
| (54) | 2-sec-Butylphenyl N-methylcarbamate |
| (55) | 3-Methylphenyl N-methylcarbamate |
| (56) | 3,4-Dimethylphenyl N-methylcarbamate |
| (57) | 2-Isopropoxyphenyl N-methylcarbamate |
| (58) | 5-Ethoxy-3-trichloromethyl-1,2,4-thiadiazole |
| (59) | O,O-Diisopropyl-S-benzyl phosphorothiolate |
| (60) | O-Ethyl-S,S-diphenyl dithiophospate |
| (61) | Polyoxin |
| (62) | Blasticidin S |
| (63) | 3,4-Dichloropropionanilide |
| (64) | Isopropyl N-(3-chlorophenyl)carbamate |
| (65) | Ethyl-di-n-propyl thiocarbamate |
| (66) | 3-Methoxycarbonylaminophenyl N-(3-methylphenyl)carbamate |
| (67) | 2-Chloro-(2,6-diethyl-N-methoxymethyl)-acetanilide |
| (68) | α,α,α-TRifluoro-2,6-dinitro-N,N-dipropyl-p-toluidine |
| (69) | S-(4-Chlorophenyl)methyl-N,N-diethylthiol carbamate |
| (70) | S-Ethylhexahydro-1H-azepine-1-carbothioate |
| (71) | N-Butoxymethyl-2-chloro-(2,6-diethyl-acetanilide |
| (72) | O-Ethyl-O-(5-methyl-2-nitrophenyl)-sec-butylphosphoramidothioate |
| (73) | N-(Chloroacetyl)-N-(2,6-diethylphenyl)-glycine ethyl ester |
| (74) | 2-[1-Methyl-2-(4-phenoxyphenoxy)-ethoxy]-pyridine |

These pesticides are contained generally in a range of 0.1 to 89 wt%, preferably in a range of 10 to 80 wt%, based on the total weight of the composition.

In the present invention, the oil content composed of pesticides, organic solvents and surfactants in the total weight of the composition is generally in a range of 10 to 90 wt%, preferably in a range of 20 to 80 wt%, based on the total weight of the composition. When the oil content exceeds 90 wt%, the emulsifiable pesticidal solid compositions obtained become wet, so that large quantities of the compositions sometimes adhere to the inside wall of a chamber in a spray drier, and the oil might be exudated during the storage. On the other hand, when the oil content is less than 10 wt%, the content of the pesticide is too low to efficiently use the compositions.

The emulsifiable pesticidal solid compositions in accordance with the present invention can be prepared, for example, as follows.

Pesticides are mixed with surfactants and if necessary, organic solvents are added to the mixture. The mixture is heated at 40 to 80° C. to dissolve, whereby an oil phase portion is prepared. On the other hand, dextrin and/or lactose and if necessary, surfactants and water soluble carriers are added to an equimolar or about 2-fold amount of water based on the total solid content (final preparation), and the mixture is heated at 40 to 80° C. to dissolve, whereby an aqueous phase portion is prepared. While heating the aqueous phase portion, the aforesaid oil phase portion is added to the aqueous phase portion by small portions to emulsify, with stirring with a homonmixer or the like. The resulting aqueous emulsion is spray-dried using a hot air spray drier to give the emulsifiable pesticidal solid compositions. The spray drier used for spray-drying is an apparatus for obtaining dry granulated grains in which liquid materials are sprayed onto heated air counter or parallel flow to move heat and substances between the liquid droplets and the air flow. As long as an apparatus has such a function, any device can be used without being limited to any particular model. Examples of the apparatus which can be used include apparatuses of horizontal parallel flow type, vertically descending parallel flow type, vertically ascending counter flow type, mixed flow type, etc. As the sprayer, a compressed nozzle, a rotary disc and a binary flow nozzle and the like are representative but various sprayers can be used depending upon purpose.

By varying conditions for spray drying, the emulsifiable pesticidal solid compositions can be obtained in a powdery form or in a granular form.

The emulsifiable pesticidal solid compositions obtained by spray drying may also be subjected to granulation, thereby obtaining granules or tablets. For granulating, there are ordinary fluid bed granulation, agitating granulation, extrusion granulation, compaction granulation, etc. Of these, fluid bed granulation and agitating granulation are particularly preferred in view of physical properties of the obtained products.

EXAMPLES

Hereafter the present invention is described in more detail by referring to the preparation examples and test examples but is not deemed to be limited only thereto In the following preparation examples, parts are all by weight in the total weight of the composition, unless otherwise indicated.

PREPARATION EXAMPLE 1

Twenty parts of Compound No. (3), 5 parts of SORPOL ®3598 (surfactant, manufactured by Toho Chemical Co., Ltd.) and 40 parts of HISOL ® SAS-296 (organic solvent or phenylxylylethane, manufactured by Nippon Petrochemicals Co., Ltd.) were heated to about 50° C. to prepare an oil phase portion. On the other hand, 35 parts of PINE-DEX ® #2 (dextrin, DE of 10 to 12, manufactured by Matsutani Kagaku Kogyo Co., Ltd.) were dissolved in 200 parts of water heated at about 50° C. While stirring, the aforementioned oil phase portion was added to the solution by small portions to give an aqueous emulsion.

The resulting aqueous emulsion was dried at a hot air inlet temperature of about 150° C. and an outlet temperature of about 60–70° C. under a spraying pressure of 1.5 kg/cm² using a hot air parallel flow spray drier (Pulvis Mini Spray Model GB-21, manufactured by Yamato Science Co., Ltd.). Thus, an emulsifiable pesticidal solid composition was obtained in a powdery form.

PREPARATION EXAMPLE 2

An emulsifiable pesticidal solid composition was obtained in a powdery form in a manner similar to Preparation Example 1 except that 35 parts of hydrated α-lactose were used in place of 35 parts of PINE-DEX ®#2.

PREPARATION EXAMPLE 3

An emulsifiable pesticidal solid composition was obtained in a powdery form in a manner similar to Preparation Example 1 except that 32 parts of PINE-DEX ®#2 and 3 parts of gum arabic were used in place of 35 parts of PINE-DEX ®#2.

PREPARATION EXAMPLE 4

An emulsifiable pesticidal solid composition was obtained in a powdery form in a manner similar to Preparation Example 1 except that 32 parts of PINE-DEX ®#2 and 3 parts of GOSENOL ® (polyvinyl alcohol, manufactured by Nippon Synthetic Chemical Industry Co., Ltd.) were used in place of 35 parts of PINE-DEX ® #2.

PREPARATION EXAMPLE 5

An emulsifiable pesticidal solid composition was obtained in a powdery form in a manner similar to Preparation Example 1 except that 32 parts PINE-DEX ® #2 and 3 parts of CELOGEN ® 7A (sodium carboxymethyl cellulose, manufactured by Dai-ichi Kogyo Seiyaku Co., Ltd.) were used in place of 35 parts of PINE-DEX ® #2.

PREPARATION EXAMPLE 6

An emulsifiable pesticidal solid composition was obtained in a powdery form in a manner similar to Preparation Example 1 except that 32 parts of PINE-DEX ®#2 and 3 parts of METLOSE ® SM-15 (methyl cellulose, manufactured by The Shin-Etsu Chemical Co., Ltd.) were used in place of 35 parts of PINE-DEX ® #2.

PREPARATION EXAMPLE 7

An emulsifiable pesticidal solid composition was obtained in a powdery form in a manner similar to Preparation Example 1 except that 35 parts of MAX ® 1000 (dextrin, DE of about 8, manufactured by Matsutani Kagaku Kogyo Co., Ltd.) were used in place of 35 parts of PINE-DEX ® #2.

PREPARATION EXAMPLE 8

An emulsifiable pesticidal solid composition was obtained in a powdery form in a manner similar to Preparation Example 1 except that 35 parts of TK-16 (dextrin, DE of 18-20, manufactured by Matsutani Kagaku Kogyo Co., Ltd.) were used in place of 35 parts of PINE-DEX ®#2.

PREPARATION EXAMPLE 9

An emulsifiable pesticidal solid composition was obtained in a powdery form in a manner similar to Preparation Example 1 except that 20 parts of Compound No. (2) were used in place of 20 parts of Compound No. (3).

PREPARATION EXAMPLE 10

An emulsifiable pesticidal solid composition was obtained in a powdery form in a manner similar to Preparation Example 1 except that 25 parts of Compound No. (3), 50 parts of HISOL ® SAS-296 and 20 parts of PINE-DEX ® #2 were used in place of 20 parts of Compound No. (3), 40 parts of HISOL ® SAS-296 and 35 parts of PINE-DEX ® #2, respectively.

PREPARATION EXAMPLE 11

An emulsifiable pesticidal solid composition was obtained in a powdery form in a manner similar to Preparation Example 10 except that 35 parts of Compound No. (3) and 10 parts of PINE-DEX ® #2 were used in place of 25 parts of Compound No. (3) and 10 parts of PINE-DEX ®#2, respectively.

PREPARATION EXAMPLE 12

An emulsifiable pesticidal solid composition was obtained in a powdery form in a manner similar to Preparation Example 10 except that 50 parts of Compound No. (4) and 25 parts of HISOL ® SAS-296 were used in place of 25 parts of Compound No. (3) and 25 parts of HISOL ® SAS-296, respectively.

PREPARATION EXAMPLE 13

Seventy five parts of Compound No. (41) and 5 parts of SORPOL ® 355LSA (surfactant, manufactured by Toho Chemical Co., Ltd.) were heated to about 50° C. to prepare an oil phase portion. On the other hand, 20 parts of PINE-DEX ® #2 were dissolved in 200 parts of water heated at about 50° C. While stirring, the aforementioned oil phase portion was added to the solution by small portions to give an aqueous emulsion.

The resulting aqueous emulsion was spray-dried by the procedure in a manner similar to Preparation Example 1 to give an emulsifiable pesticidal solid composition in a powdery form.

PREPARATION EXAMPLE 14

An emulsifiable pesticidal solid composition was obtained in a powdery form in a manner similar to Preparation Example 1 except that 35 parts of PINE-FLOW ®(dextrin, DE of 7 to 9, granular form because of the product dried by a drum drier, manufactured by Matsutani Chemical Co., Ltd.) were used in place of 35 parts of PINE-DEX ® #2.

PREPARATION EXAMPLE 15

An emulsifiable pesticidal solid composition was obtained in a powdery form in a manner similar to Preparation Example 1 except that 20 parts of Compound No. (6) were used in place of 20 parts of Compound No. (3).

PREPARATION EXAMPLE 16

An emulsifiable pesticidal solid composition was obtained in a powdery form in a manner similar to Preparation Example 1 except that 30 parts of Compound No. (6) and 30 parts of HISOL ® SAS-296 were used in place of 20 parts of Compound No. (3) and 40 parts of HISOL ® SAS-296, respectively.

PREPARATION EXAMPLE 17

An emulsifiable pesticidal solid composition was obtained in a powdery form in a manner similar to Preparation Example 1 except that 20 parts of Compound No.

(74) were used in place of 20 parts of Compound No. (3).

PREPARATION EXAMPLE 18

An emulsifiable pesticidal solid composition was obtained in a powdery form in a manner similar to Preparation Example 16 except that 30 parts of Compound No. (74) were used in place of 30 parts of Compound No. (6).

PREPARATION EXAMPLE 19

An emulsifiable pesticidal solid composition was obtained in a powdery form in a manner similar to Preparation Example 13 except that 10 parts of Compound No. (5), 10 parts of SORPOL ® 3598 and 80 parts of PINE-DEX ®#2 were used in place of 75 parts of Compound No. (41), 5 parts of SORPOL ®355LSA and 20 parts of PINE-DEX ®#2.

PREPARATION EXAMPLE 20

An emulsifiable pesticidal solid composition was obtained in a powdery form in a manner similar to Preparation Example 19 except that 40 parts of Compound No. (5) and 50 parts of PINE-DEX ® #2 were used in place of 10 parts of Compound No. (5) and 80 parts of PINE-DEX ®#2.

PREPARATION EXAMPLE 21

An emulsifiable pesticidal solid composition was obtained in a powdery form in a manner similar to Preparation Example 1 except that 20 parts of HISOL ® SAS-296 and 55 parts of MAX ® 1000 were used in place of 40 parts of HISOL ® SAS-296 and 35 parts of PINE-DEX ® #2, respectively and a dry hot air inlet temperature was set at about 120° C.

PREPARATION EXAMPLE 22

An emulsifiable pesticidal solid composition obtained in a powdery form in Preparation Example 21 was put on a fluid bed dry granulating machine (Model STREA-1, manufactured by POWLEX Co., Ltd. (previous name: Fuji Sangyo Co., Ltd.,). While controlling an inlet temperature of about 70° C. and an outlet temperature of about 40 to about 50° C., 10% aqueous solution of MAX ® 1000 was sprayed and granulated to give an emulsifiable pesticidal solid composition in a granular form.

COMPARATIVE EXAMPLE 1

Twenty parts of Compound No. (3), 5 parts of SORPOL ® 3598 and 40 parts of HISOL ® SAS-296 were heated at about 50° C. to dissolve. While stirring, the solution was charged in a beaker charged with 35 parts of PINEFLOW ® and the mixture was stirred for further 10 minutes. However, the resulting mixture was in a wet state and extremely sticky so that a fluidizable product was not obtained.

COMPARATIVE EXAMPLE 2

Seventy five parts of Compound No. (41) and 5 parts of SORPOL ® 355LSA were heated at about 50° C. to dissolve. While stirring, the solution was charged in a beaker charged with 20 parts of PINEFLOW ® and the mixture was stirred for further 10 minutes. However, the resulting mixture was in a wet state and extremely sticky so that a fluidizable product was not obtained.

COMPARATIVE EXAMPLE 3

The procedure was carried out in a manner similar to Comparative Example 1 except that 35 parts of PINE-DEX ® #2 were used in place of 35 parts of PINE-FLOW ®. However, a fluidizable product was not obtained as in Comparative Example 1.

COMPARATIVE EXAMPLE 4

Thirty parts of Compound No. (41) and 5 parts of SORPOL ® 355LSA were heated at about 50° C. to dissolve. While stirring, the solution was charged in a beaker charged with 65 parts of PINEFLOW ® and the mixture was stirred for further 10 minutes. The oil component was almost absorbed onto the carriers. However, the resulting mixture was extremely sticky so that a fluidizable product was not obtained.

COMPARATIVE EXAMPLE 5

Forty parts of Compound No. (5) were heated to about 50° C. to prepare an oil phase portion. On the other hand, 60 parts of PINE-DEX ® #2 were dissolved in 200 parts of water heated at about 50° C. While stirring, the aforementioned oil phase portion was added to the solution by small portions. However, the mixture was not emulsified but the oil phase was separated from the aqueous phase so that it was impossible to spray dry the mixture.

COMPARATIVE EXAMPLE 6

The procedure was carried out in a manner similar to Preparation Example 1 except that 35 parts of saccharose were used in place of 35 parts of PINE-DEX ®#2. However, the oil was adhered to a chamber of the spray drier and an emulsifiable pesticidal solid composition in a powdery form was not obtained.

COMPARATIVE EXAMPLE 7

The procedure was carried out in a manner similar to Preparation Example 20 except that 50 parts of sodium casein and 500 parts of water heated at about 50° C. were used in place of 50 parts of PINE-DEX ® #2 and 200 parts of water heated at about 50° C. However, the oil was adhered to a chamber of the spray drier and an emulsifiable pesticidal solid composition in a powdery form was not obtained.

The emulsifiable pesticidal solid compositions obtained in Preparation Examples 1 through 22 were all in a dry state and showed good flowability.

To the contrary, the compositions obtained in Comparative Examples 1 through 7 were all sticky and fluidizable emulsifiable pesticidal solid compositions could not be obtained.

TEST EXAMPLE 0.5 g each of the emulsifiable pesticidal solid compositions produced in Preparation Examples 1 through 22 were charged in a 250 ml glass stoppered cylinders, each of which contained 100 ml of 3 hard water (53.4 ppm hard water as CaO). Inversion of the cylinder was repeated 30 times at a rate of one per 2 seconds to emulsify. The powders were fully dissolved in all of the compositions. Then, each cylinder was kept for 15 minutes in a thermostat at 20° C. to examine stability of the emulsion. In any case, isolated oil cream was hardly observed.

The emulsifiable pesticidal solid compositions in accordance with the present invention maintain the preparation form which are not sticky, provides good flowability and are easy in handling, even in the compositions containing the oil components in large quantities which were prepared in the past only with difficulty. In addition, the emulsifiable solid compositions are readily emulsified when diluted with water. Furthermore, the emulsifiable solid compositions are excellent in emulsion stability.

What is claimed is:

1. An emulsifiable pesticidal solid composition prepared by spray dry method from an aqueous emulsion comprising:
    (a) a pesticide having a melting point of not higher than 70° C.
    (b) surfactant,
    (c) dextrin and/or lactose, and
    (d) water, and,
    (e) optionally an organic solvent and/or a water soluble carrier,
    wherein said pesticide, surfactant and dextrin and/or lactose are contained in amounts of 10 to 80 wt%, 1 to 10 wt% and 10 to 80 wt%, respectively, based on the total weight of the composition.

2. A process for preparing an emulsifiable pesticidal solid composition which comprises spray-drying an aqueous emulsion comprising:
    (a) a pesticide having a melting point of not higher than 70° C.,
    (b) surfactant,
    (c) dextrin and/or lactose, and
    (d) water, and,
    (e) optionally an organic solvent and/or a water soluble carrier,
    wherein said pesticide, surfactant and dextrin and/or lactose are contained in amounts of 10 to 80 wt%, 1 to 10 wt% and 10 to 80 wt%, respectively, based on the total weight of the composition.

3. A granulated emulsifiable pesticidal solid composition, wherein an emulsifiable pesticidal solid composition as claimed in claim 1 is granulated.

4. A process for preparing a granulated emulsifiable pesticidal solid composition which comprises granulating an emulsifiable pesticidal solid composition as claimed in claim 1.

5. A method for controlling harmful organisms or regulating plant growth using an emulsifiable pesticidal solid composition as claimed in claim 1.

6. A method for controlling harmful organisms or regulating plant growth using an emulsifiable pesticidal solid composition as claimed in claim 4.

* * * * *